United States Patent
Lyu et al.

(10) Patent No.: US 11,690,569 B2
(45) Date of Patent: Jul. 4, 2023

(54) BLOOD VESSEL DETECTING APPARATUS AND IMAGE-BASED BLOOD VESSEL DETECTING METHOD

(71) Applicants: Acer Incorporated, New Taipei (TW); Far Eastern Memorial Hospital, New Taipei (TW)

(72) Inventors: Yun-Huan Lyu, New Taipei (TW); Cheng-Tien Hsieh, New Taipei (TW); Ai-Hsien Li, New Taipei (TW); Wen-Po Chuang, New Taipei (TW)

(73) Assignees: Acer Incorporated, New Taipei (TW); Far Eastern Memorial Hospital, New Taipei (TW)

( * ) Notice: Subject to any disclaimer, the term of this patent is extended or adjusted under 35 U.S.C. 154(b) by 230 days.

(21) Appl. No.: 17/145,405

(22) Filed: Jan. 11, 2021

(65) Prior Publication Data

US 2022/0167912 A1    Jun. 2, 2022

(30) Foreign Application Priority Data

Nov. 30, 2020   (TW) .................................. 109142116

(51) Int. Cl.
*G06K 9/00*    (2022.01)
*A61B 5/00*    (2006.01)
(Continued)

(52) U.S. Cl.
CPC ............ *A61B 5/489* (2013.01); *A61B 5/7264* (2013.01); *G06T 7/11* (2017.01); *G06T 7/149* (2017.01);
(Continued)

(58) Field of Classification Search
CPC ...................................................... A61B 5/489
See application file for complete search history.

(56) References Cited

U.S. PATENT DOCUMENTS

| | | | |
|---|---|---|---|
| 10,937,549 B2 * | 3/2021 | Ma ........................ | A61B 5/0261 |
| 2015/0339459 A1 * | 11/2015 | Taylor .................. | A61B 5/7278 |
| | | | 703/9 |

(Continued)

FOREIGN PATENT DOCUMENTS

| | | |
|---|---|---|
| CN | 109074870 | 12/2018 |
| CN | 106548213 | 4/2019 |

(Continued)

*Primary Examiner* — Oneal R Mistry
(74) *Attorney, Agent, or Firm* — JCIPRNET

(57) ABSTRACT

A blood vessel detecting apparatus and an image-based blood vessel detecting method are provided. In the method, first to-be-evaluated data is detected through a first detecting model to obtain a first detection result. Second to-be-evaluated data is detected through a second detecting model to obtain a second detection result. The first to-be-evaluated data includes one or more medical images obtained from photographing a blood vessel. The first detection result output by the first detecting model includes one or more pixels in the medical image belonging to the blood vessel. The first detecting model and the second detecting model are constructed based on a machine learning algorithm. The second to-be-evaluated data includes the first detection result. The second detection result output by the second detecting model includes one or more pixels in the medical image belonging to the blood vessel.

12 Claims, 10 Drawing Sheets

(51) Int. Cl.
  *G06T 7/149* (2017.01)
  *G06T 7/11* (2017.01)
(52) U.S. Cl.
  CPC .............. *G06T 2207/30096* (2013.01); *G06T 2207/30101* (2013.01)

(56) References Cited

U.S. PATENT DOCUMENTS

| | | | | |
|---|---|---|---|---|
| 2017/0071479 | A1* | 3/2017 | Kano | A61B 5/026 |
| 2017/0076014 | A1* | 3/2017 | Bressloff | A61F 2/915 |
| 2022/0230310 | A1* | 7/2022 | Xie | G06V 10/758 |
| 2022/0296205 | A1* | 9/2022 | Kang | G16H 50/70 |

FOREIGN PATENT DOCUMENTS

| | | |
|---|---|---|
| CN | 110288611 | 9/2019 |
| TW | 201903708 | 1/2019 |
| TW | 202008211 | 2/2020 |
| TW | I698225 | 7/2020 |
| TW | I711051 | 11/2020 |
| WO | 2018001099 | 1/2018 |

* cited by examiner

BLOOD VESSEL DETECTING APPARATUS AND IMAGE-BASED BLOOD VESSEL DETECTING METHOD

CROSS-REFERENCE TO RELATED APPLICATION

This application claims the priority benefit of Taiwanese application no. 109142116, filed on Nov. 30, 2020. The entirety of the above-mentioned patent application is hereby incorporated by reference herein and made a part of this specification.

BACKGROUND

Technical Field

The disclosure relates to an image recognition technology; particularly, the disclosure relates to a blood vessel detecting apparatus and an image-based blood vessel detecting method.

Description of Related Art

Vascular images serve as a basis in determining a lesion for a variety of diseases. When a doctor makes diagnoses based on the vascular images, subjectivity is often incorporated, generating deviations in the diagnoses. Besides, manual interpretation is also a time-consuming and costly process. Moreover, from the perspective of the patient, the entire diagnostic process seems like a black box, where the patient cannot understand how the diagnostic result is obtained, thus leading to poor communication and generating disputes.

Existing blood vessel segmentation technologies include the calculation method, in which analyses are performed based on intensity of each pixel on an image. For example, a second-order partial differential calculation is performed on the pixel relative to two dimensions of the image, and then based on eigenvectors and eigenvalues of an obtained second-order partial differential matrix, whether the pixel belongs to a blood vessel or not is determined. However, in addition to the multitude of blood vessel forms, the blood vessel on which the vascular medical image angiography is performed may already be ill-conditioned, which increases the degree of difference between blood vessels, so that the determination based on the eigenvectors and the eigenvalues cannot cover the various blood vessel forms. Moreover, this method is limited to a small-scale determination, without considering large-scale information.

SUMMARY

The embodiments of the disclosure provide a blood vessel detecting apparatus and an image-based blood vessel detecting method, which accurately detect a blood vessel in a vascular image.

The image-based blood vessel detecting method according to an embodiment of the disclosure includes (but is not limited to) the following steps. First to-be-evaluated data is detected through a first detecting model to obtain a first detection result. Second to-be-evaluated data is detected through a second detecting model to obtain a second detection result. The first detecting model is constructed based on a machine learning algorithms. The first to-be-evaluated data includes one or more medical images obtained from photographing a blood vessel. The first detection result output by the first detecting model includes one or more pixels of the medical image belonging to the blood vessel. The second detecting model is constructed based on a machine learning algorithm. The second to-be-evaluated data includes the first detection result. The second detection result output by the second detecting model includes one or more pixels of the medical image belonging to the blood vessel.

The blood vessel detecting apparatus according to an embodiment of the disclosure includes (but is not limited to) a storage device and a processor. The storage device stores program codes. The processor is coupled to the storage device and configured to load and execute the program codes to detect first to-be-evaluated data through a first detecting model to obtain a first detection result, and detect second to-be-evaluated data through a second detecting model to obtain a second detection result. The first detecting model is constructed based on a machine learning algorithm. The first to-be-evaluated data includes one or more medical images obtained from photographing a blood vessel. The first detection result output by the first detecting model includes one or more pixels of the medical image belonging to the blood vessel. The second detecting model is constructed based on a machine learning algorithm. The second to-be-evaluated data includes the first detection result. The second detection result output by the second detecting model includes one or more pixels of the medical image belonging to the blood vessel.

Based on the foregoing, according to the embodiment of the disclosure, the blood vessel detecting apparatus and the image-based blood vessel detecting method provide a multi-stage blood vessel detecting mechanism, and adopt the previous detection result as the input data of the subsequent detecting model to increase the accuracy of identification.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Figure 1:
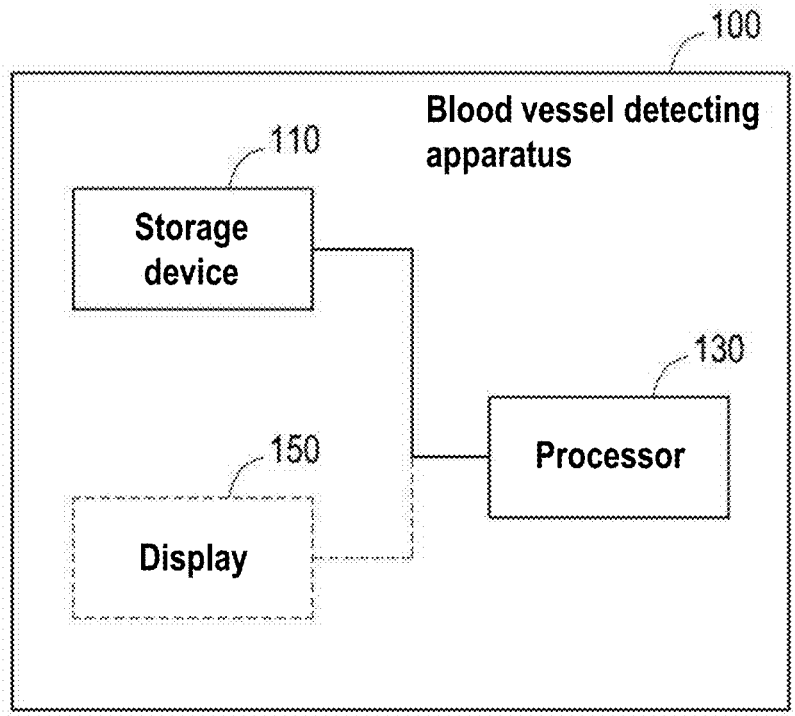
FIG. 1 is a block diagram of elements of a blood vessel detecting apparatus according to an embodiment of the disclosure.

FIG. 1 is a block diagram of elements of a blood vessel detecting apparatus 100 according to an embodiment of the disclosure. With reference to FIG. 1, the blood vessel detecting apparatus 100 includes (but is not limited to) a storage device 110 and a processor 130. The blood vessel detecting apparatus 100 may include a desktop computer, a notebook computer, a smart phone, a tablet computer, a server, a medical testing instrument, or other computational apparatuses.

The storage device 110 may include a fixed or removable element in any form, such as a random access memory (RAM) device, a read only memory (ROM) device, a flash memory device, a traditional hard disk drive (HDD), a solid-state drive (SSD), or the like. In an embodiment, the storage device 110 is configured to record program codes, software modules, configuration, data, or files.

The processor 130 is coupled to the storage device 110, and the processor 130 may also include a central processing unit (CPU), a graphic processing unit (GPU), or any other programmable general-purpose or special-purpose microprocessor, digital signal processor (DSP), programmable controller, field programmable gate array (FPGA), application-specific integrated circuit (ASIC), neural network accelerator, other similar elements, or a combination of the above elements. In an embodiment, the processor 130 is configured to execute all or some operations of the blood vessel detecting apparatus 100, and may load and execute the program codes, software modules, files, and data recorded in the storage device 110.

In some embodiment, the blood vessel detecting apparatus 100 further includes a display 150. The display 150 may include a liquid-crystal display (LCD), a light-emitting diode (LED) display, an organic light-emitting diode (OLED), a quantum dot display, or other types of display. In an embodiment, the display 150 is configured to display a medical image or a processed medical image.

Hereinafter, a method according to an embodiment of the disclosure will be described in conjunction with devices, elements, and modules of the blood vessel detecting apparatus 100. Depending on the implementation condition, each procedure of the method may be accordingly adjusted, and is not limited thereto.

Figure 2:
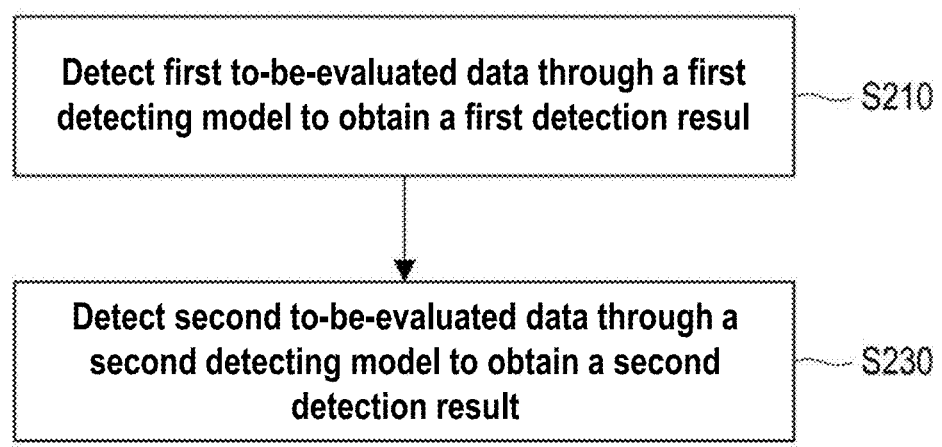
FIG. 2 is a flowchart of an image-based blood vessel detecting method according to an embodiment of the disclosure.

FIG. 2 is a flowchart of an image-based blood vessel detecting method according to an embodiment of the disclosure. With reference to FIG. 2, the processor 130 is configured to detect first to-be-evaluated data through a first detecting model to obtain a first detection result (step S210). Specifically, the first detecting model is constructed based on a machine learning algorithm. The machine learning algorithm may include a convolutional neural network (CNN), a recurrent neural network (RNN), a multi-layer perceptron (MLP), a support vector machine (SVM), or other algorithms. The machine learning algorithm analyzes training samples to obtain a pattern therein, to predict unknown data through the pattern. The detecting model is namely a machine learning model constructed after learning, and thereby inference is performed on the to-be-evaluated data. In an embodiment, the first detecting model adopts a medical image (or a vascular image) obtained from photographing a blood vessel and a result thereof annotated as belonging to the blood vessel as a training sample.

The first to-be-evaluated data includes one or more medical images obtained from photographing one or more blood vessels. It should be noted that the body part where the blood vessel is located is not limited by the embodiment of the disclosure. In addition, the first detecting model is configured to analyze the first to-be-evaluated data and output the first detection result accordingly. This first detection result may include one or more pixels in the medical image belonging to the blood vessel or not belonging to the blood vessel.

In another embodiment, the first to-be-evaluated data may include other characteristics such as a contour, a size, an edge, or the like, of the blood vessel. In some embodiments, the first to-be-evaluated data may further include the characteristics of medical images photographed at different time points on the same part.

The processor 130 is configured to detect second to-be-evaluated data through a second detecting model to obtain a second detection result (step S230). Specifically, the second detecting model is also constructed based on a machine learning algorithm. The first detecting model and the second detecting model may adopt the same or different machine learning algorithms, which is not limited by the disclosure. Different from the first to-be-evaluated data, the second to-be-evaluated data adopted as input data of the second detecting model includes the first detection result output by the first detecting model. Besides, the second detection result output by the second detecting model may include one or more pixels in the medical image belonging to the blood vessel or not belonging to the blood vessel.

In an embodiment, the processor 130 may perform image processing on the medical image, which image processing is related to augmentation of a contour of the blood vessel, such as edge augmentation processing, contrast adjustment, or other process that increases contour identifiability. The second to-be-evaluated data may further include a processed medical image. Accordingly, the features of the calculation method (e.g., increasing contour identifiability) and the learning method (e.g., machine learning) are combined, and the accuracy of the identification result is increased with less data. Besides, the augmentation of the contour of the blood vessel facilitates reduction in region discontinuity in the blood vessel detection.

Figure 3:
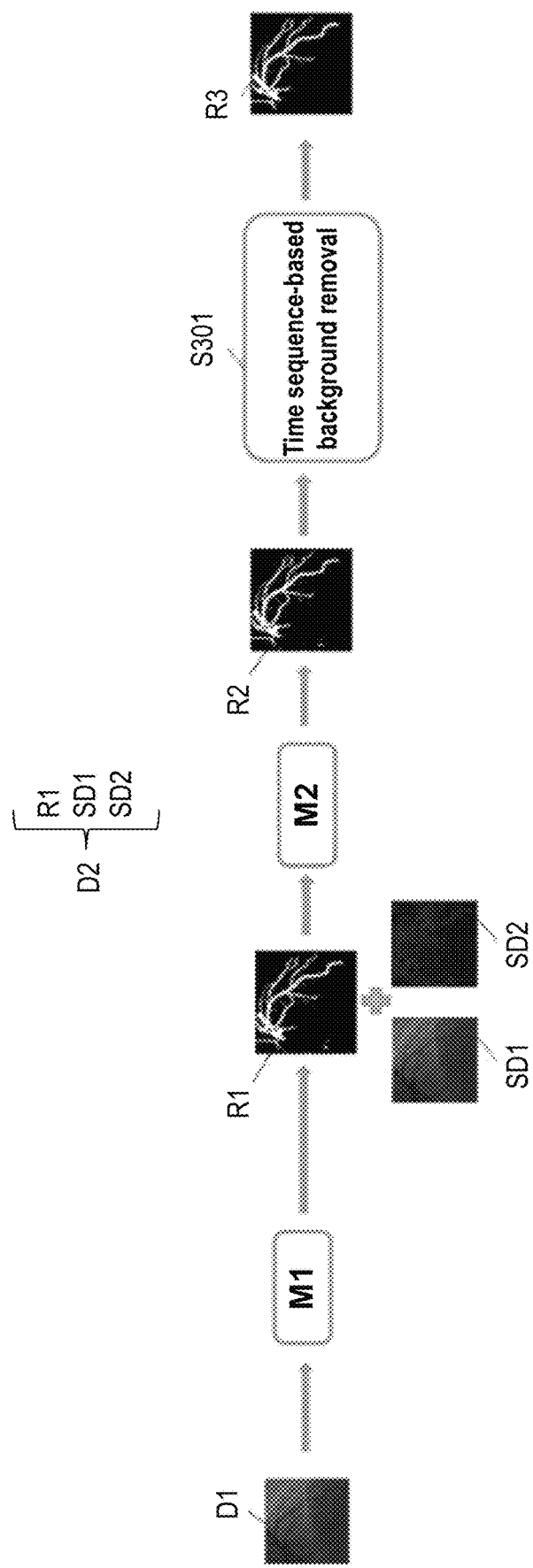
FIG. 3 is a schematic flowchart of a blood vessel detecting method according to an embodiment of the disclosure.

For example, FIG. 3 is a schematic flowchart of a blood vessel detecting method according to an embodiment of the disclosure. With reference to FIG. 3, a medical image serves as to-be-evaluated data D1 and is input to a detecting model M1 to obtain a detection result R1. Then, the detection result R1 and supplementary data SD1 and SD2 (e.g., the original medical image and an image with an augmented edge) serve as to-be-evaluated data D2 and are input to a detecting model M2 to obtain a detection result R2.

In another embodiment, the second to-be-evaluated data may include other characteristics, such as a contour, a size, a thickness, or the like, of the blood vessel. In some embodiments, the second to-be-evaluated data may further include the characteristics of medical images photographed at different time points on the same part.

In some embodiments, based on the first detection result or the second detection result of the medical image, the processor 130 may segment each medical image into one or more pixels belonging to the blood vessel to form a segmentation image, such as minimizing a gray level of the pixel belonging to the blood vessel and maximizing a gray level of the pixel not belonging to the blood vessel through binarization.

Figure 4A:
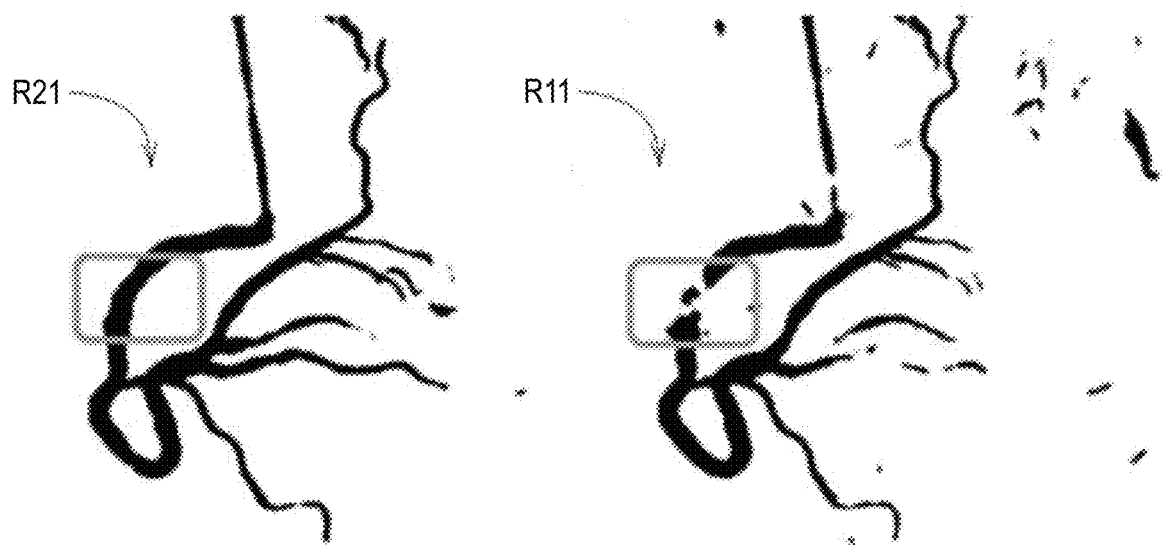
FIG. 4A and FIG. 4B show examples of comparison between the detection results.
Figure 4B:
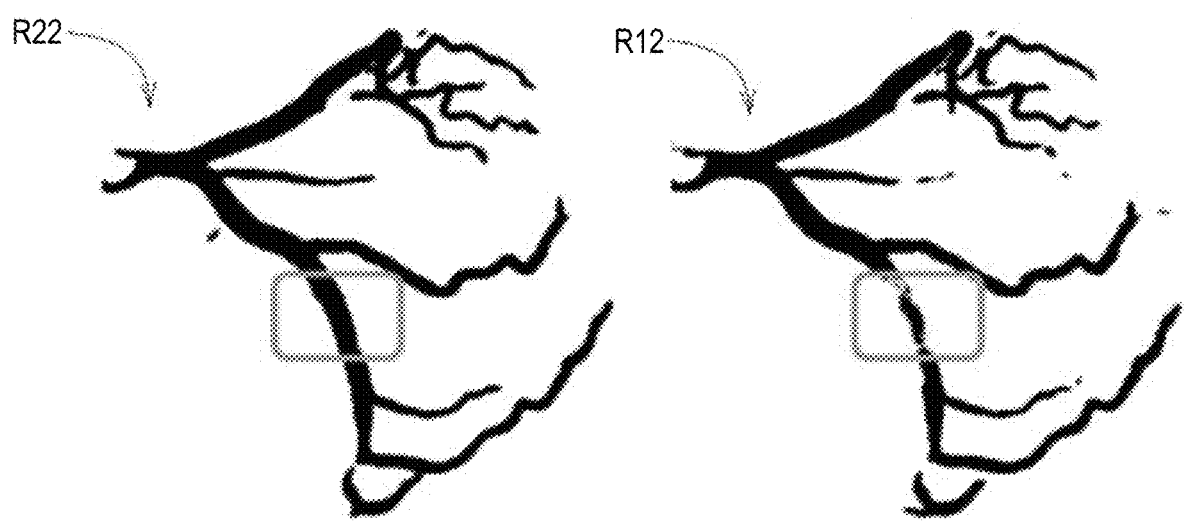

FIG. 4A and FIG. 4B show examples of comparison between the detection results. With reference to FIG. 4A and FIG. 4B, images on the left are segmentation images R21 and R22 formed based on the detection result R2, and images on the right are segmentation images R11 and R12 formed based on the detection result R1. In the rectangular boxes in the figures, it can be seen that in the segmentation images R11 and R12, discontinuity in the blood vessels is present, but in the segmentation images R21 and R22, the blood vessels have a continuous contour.

With reference to FIG. 3, the processor 130 may perform time-sequence-based background removal (step S301) on the detection result R2 to obtain a detection result R3. In an embodiment, the medical images are sorted based on a time sequence, namely medical images (or medical images of different frames) photographed at different time points at the same projection position and/or angle. Based on the second detection result of the medical images, the processor 130 may segment each medical image into one or more blood vessel regions belonging to the blood vessel to obtain a plurality of segmentation images of the medical images corresponding to different frames.

Notably, when interpreting the medical images, a doctor often refers to variance between the frames of different time sequences to increase the accuracy of the interpretation result. Based on the time sequences, the processor 130 may determine a displacement of each pixel of each blood vessel region in the segmentation images. For example, the processor 130 may adopt optical flow or other target tracking technologies to analyze the displacement (i.e., a dynamic change) of each pixel between successive frames.

The processor 130 may classify the blood vessel regions based on the displacement corresponding to each blood vessel region and a comparison result with the blood vessel region in the segmentation image of the previous frame. The comparison result is related to the displacement and an overlapping size between the blood vessel regions. For example, the processor 130 may compare the obtained displacement with the blood vessel region in the segmentation image of the previous frame or the further previous frame. The comparison result is that the two blood vessel regions most overlapping with the position of the displacement (or trajectory) will be classified into the same class (e.g., combined into one region), to further obtain the size variance of each blood vessel region in the time sequence. Accordingly, background noise in the segmentation image is removed (e.g., regions of other classes are regarded as noise). Namely, less background noise is present in the segmentation image of the detection result R3 than in the segmentation image of the detection result R2.

Figure 5:
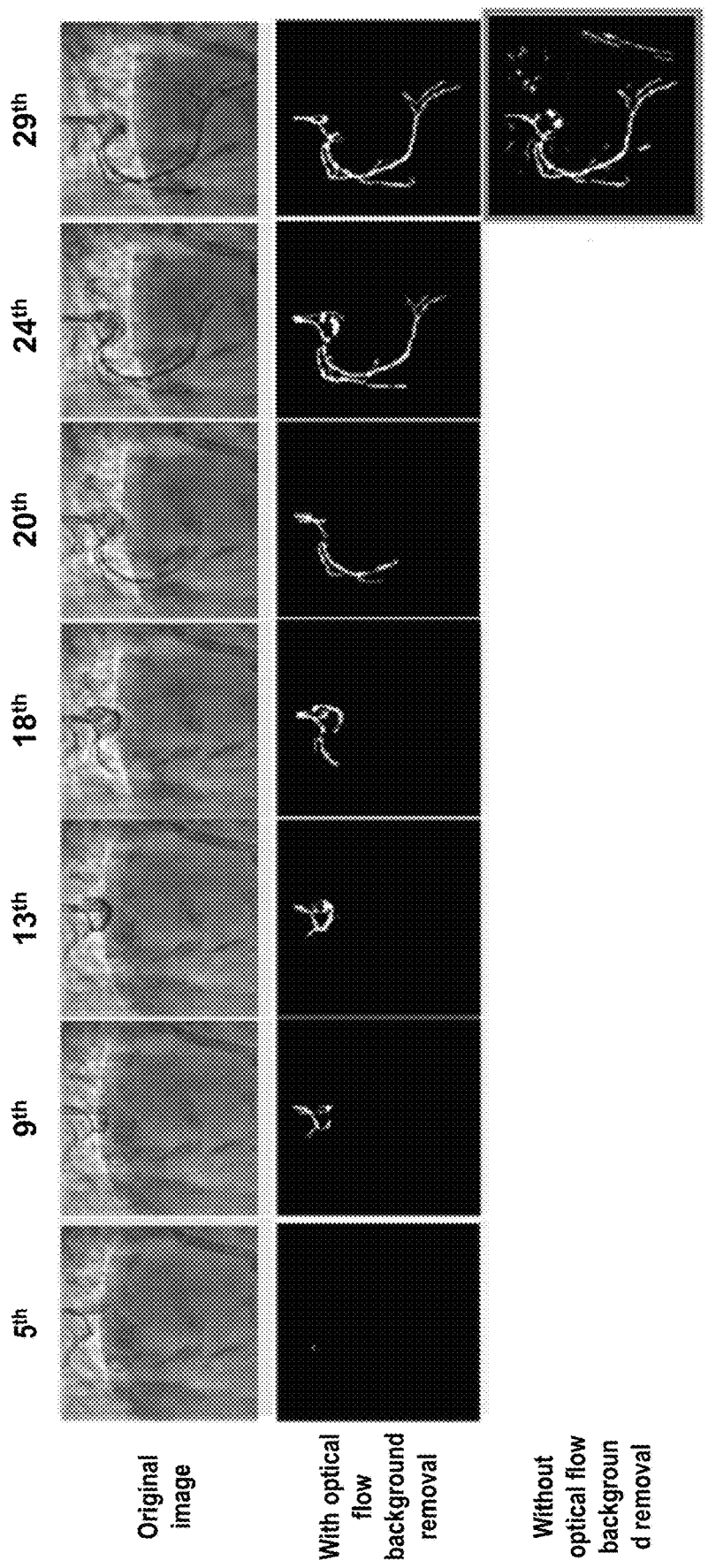
FIG. 5 is a schematic diagram of time-sequence-based target tracking according to an embodiment of the disclosure.

For example, FIG. 5 is a schematic diagram of time-sequence-based target tracking according to an embodiment of the disclosure. With reference to FIG. 5, using optical flow background removal, the shape of the blood vessel region varies between different frames. Accordingly, the complete blood vessel contour may be gradually obtained from segmentation based on the time sequence, and noise outside the blood vessel contour may be removed. However, without using the optical flow background removal, some blobs are still present outside the blood vessel contour.

Figure 6A:
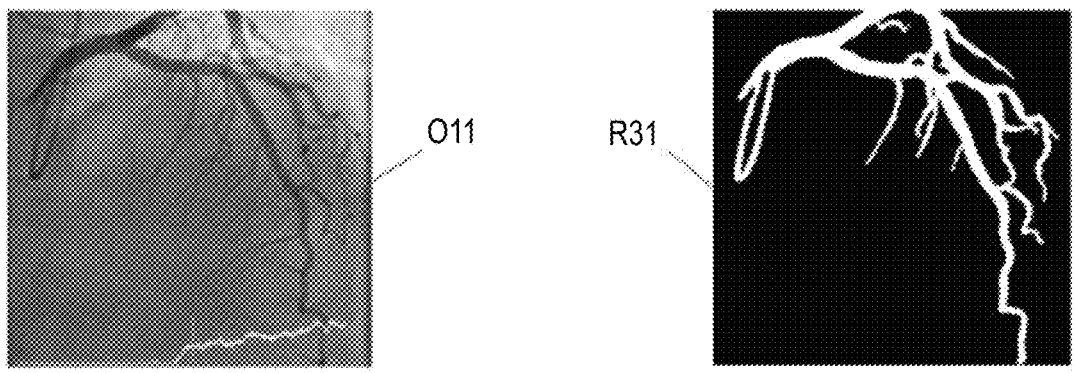
FIG. 6A-FIG. 6C show examples of comparison between medical images and detection results.
Figure 6B:
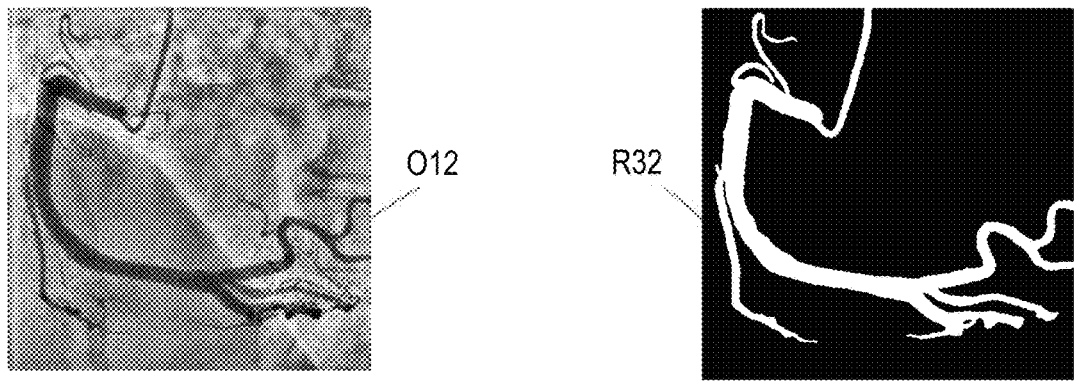
Figure 6C:
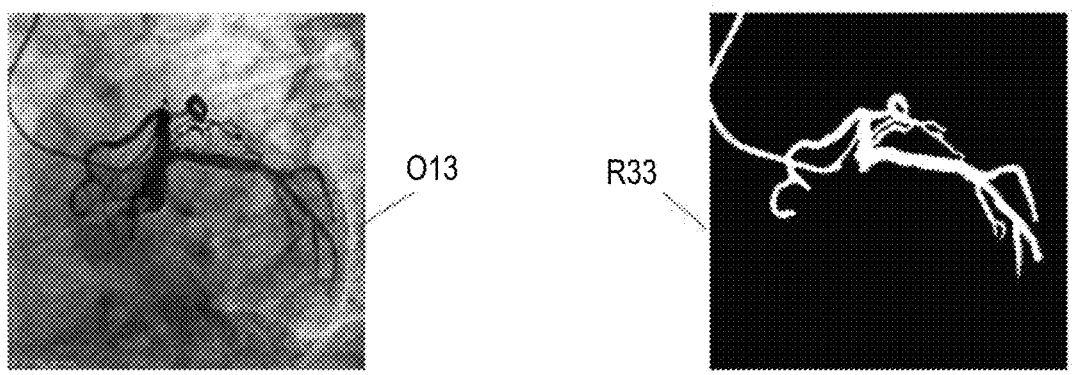

FIG. 6A-FIG. 6C show examples of comparison between medical images O11-O13 and detection results R31-R33. With reference to FIG. 6A to FIG. 6C, taking blood vessel segmentation in cardiovascular angiography as an example, the blood vessel contours of the segmentation images obtained from the detection results R31-R33 are approximately close to the medical images O11-O13, and the blood vessels are continuous without interruption.

Notably, many vascular branches may be present in the segmentation image, and some of the branches are not helpful in diagnosis. Regarding a major blood vessel, in an embodiment, the processor 130 may detect third to-be-evaluated data through a third detecting model to obtain a third detection result. Specifically, the third detecting model is also constructed based on one of the machine learning algorithms. Different from the first and second to-be-evaluated data, the third to-be-evaluated data includes the second detection result of the medical image of the current frame and the second detection result of the medical image of the previous frame (i.e., the output of the detecting model in a previous stage). Similarly, based on the relevance of blood vessels in the time sequence, the medical images of previous and subsequent frames facilitate blood vessel detection. The third detection result output by the third detecting model includes a major blood vessel in the medical image. In a learning stage, the third detecting model is trained based on a variety of training samples annotated as a specific major blood vessel (e.g., the left circumflex branch, the left anterior descending branch, etc. of the coronary artery).

Figure 7:
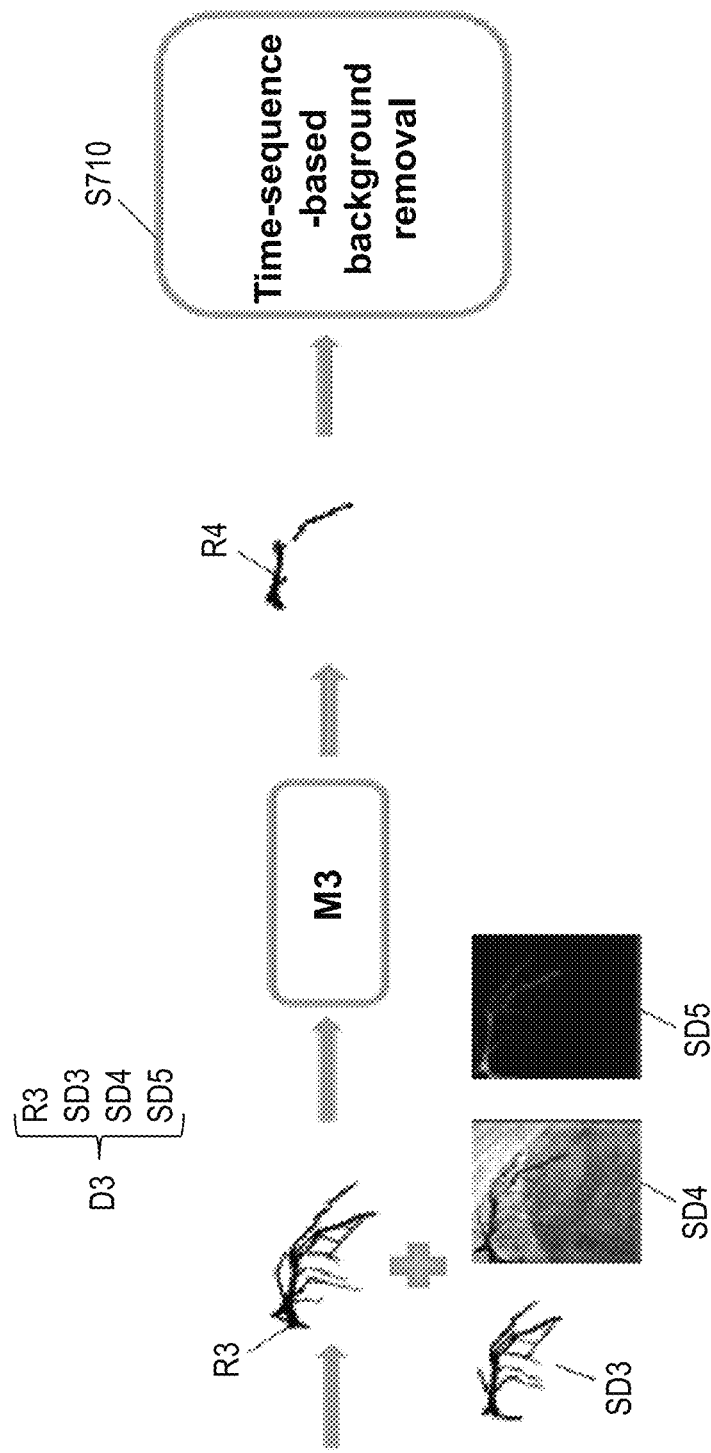
FIG. 7 is a schematic flowchart of a major blood vessel detecting method according to an embodiment of the disclosure.

For example, FIG. 7 is a schematic flowchart of a major blood vessel detecting method according to an embodiment of the disclosure. With reference to FIG. 7, after the detection result R3 is obtained as shown in FIG. 3, the detection result R3 and supplementary data SD3-SD5 (e.g., the third detection result R3 of the previous frame, the previous and subsequent frames after estimated through the optical flow, blurred, and then added with a boundary of the current frame, and the original medical image of the current frame) serve as to-be-evaluated data D3 and are input to a detecting model M3 to obtain a detection result R4. At this time, the segmentation image corresponding to the detection result R4 only includes the major blood vessel, and other branches are regarded as background and removed.

It should be noted that the major blood vessel may be determined based on a weight that evaluates a lesion complexity of a plurality of blood vessel segments. Taking SYNTAX score as an example, the right coronary artery may be divided into the proximal end of the right coronary artery, the middle end of the right coronary artery, the distal end of the right coronary artery, the right posterior descending branch, the right posterior branch, and other blood vessel segments. The lesion complexity is quantitatively evaluated based on anatomical characteristics such as a location, severity, bifurcation, and calcification of the lesion, and each blood vessel segment is assigned a corresponding weight. The value of the weight is associated with the identification of the major blood vessel. For example, one having a weight greater than a specific threshold (e.g., 0.8, 1, 1.2, etc.) is a major blood vessel, while one having a weight less than the specific threshold is not a major blood vessel. However, the major blood vessel is not limited to the coronary artery.

In some embodiments, the processor 130 may further perform the time-sequence-based background removal (step S710) as described in step S301 on the detection result R4 to remove additional noise.

In an embodiment, the processor 130 may determine a skeleton of the major blood vessel based on the detection result output by the second detecting model and the detection result output by the third detecting model. Specifically, the detection result of the second detecting model may serve as a global feature for reference, to further refine the blood vessel contour in the detection result output by the third detecting model.

Figure 8:
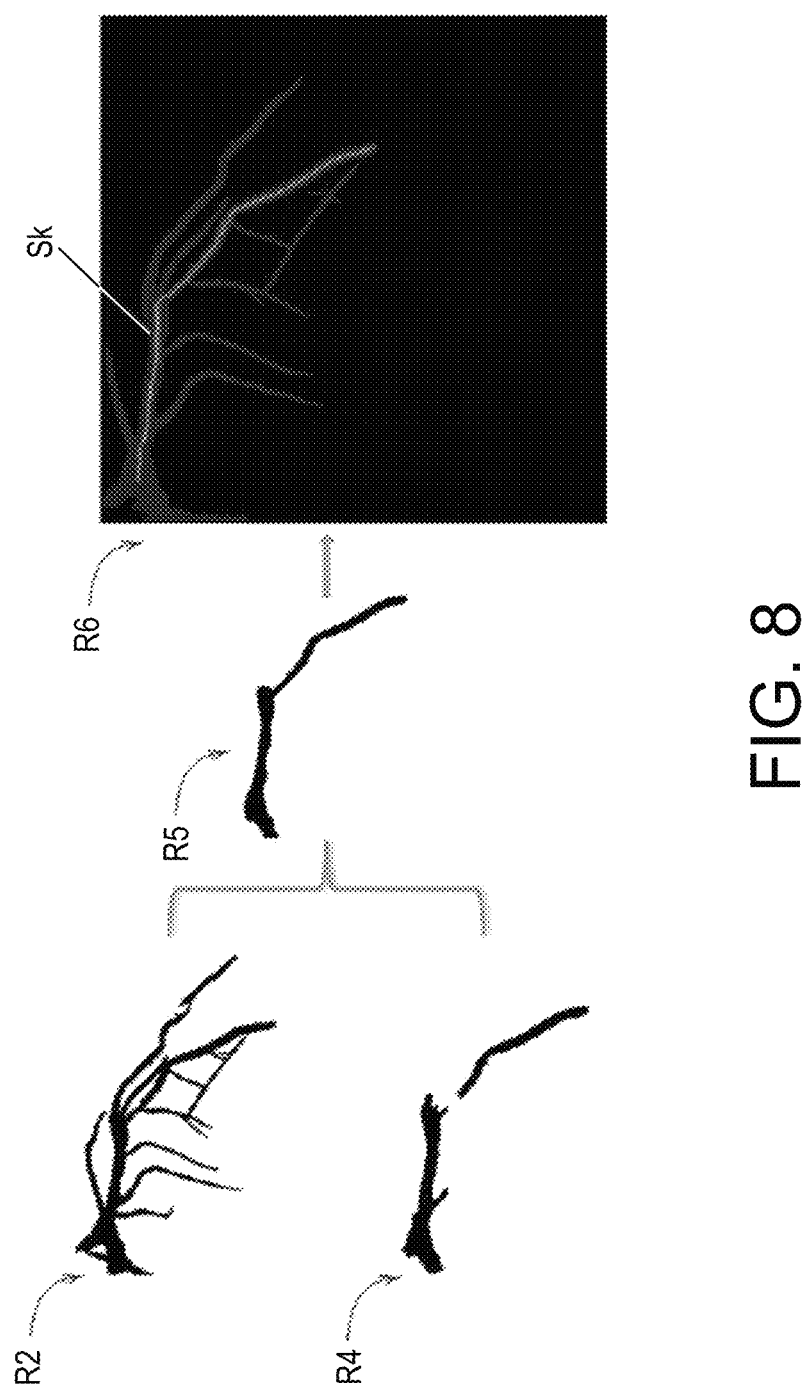
FIG. 8 shows an example of major blood vessel detection.

For example, FIG. 8 shows an example of major blood vessel detection. With reference to FIG. 8, for example, the processor 130 obtains other branches from the detection result R2, and remove the branches from the corresponding positions in the detection result R4 output by the detecting model M3 to form a detection result R5. Herein, compared with the detection result R4, the contour of the major blood vessel of the detection result R5 is continuous and absent side branches.

Figure 9:
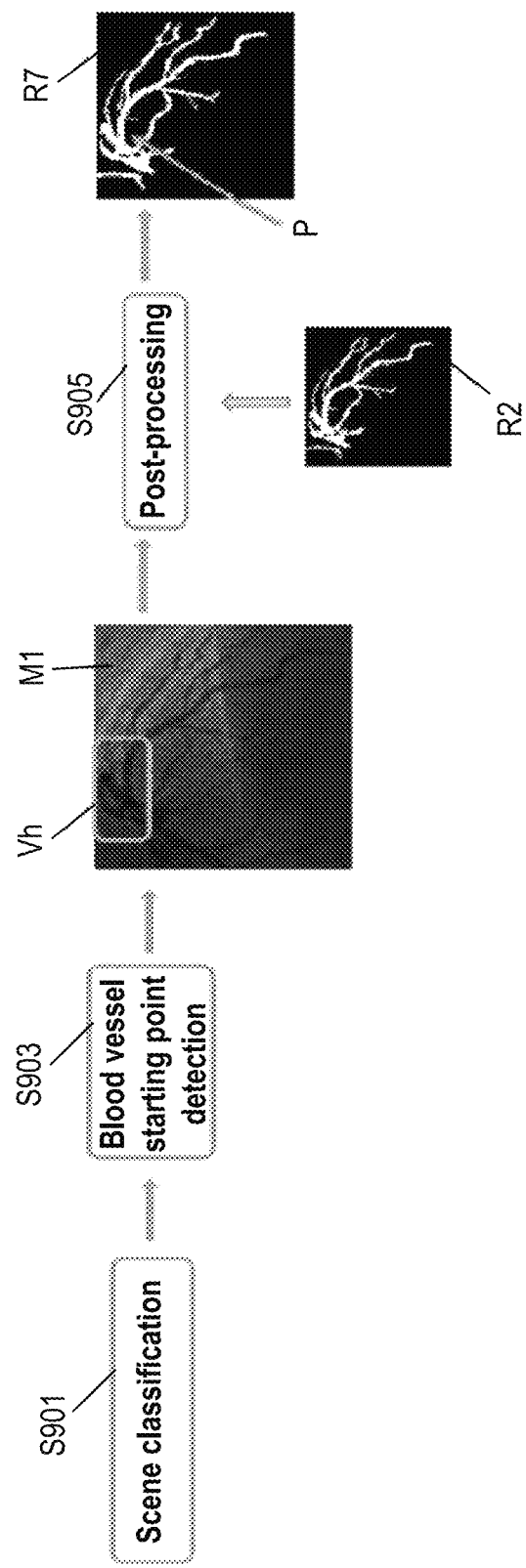
FIG. 9 is a schematic flowchart of a target blood vessel detecting method according to an embodiment of the disclosure.

Next, the processor 130 may search for the shortest path from a blood vessel starting point to a blood vessel end point, and adopt this shortest path as the skeleton. Specifically, FIG. 9 is a schematic flowchart of a target blood vessel detecting method according to an embodiment of the disclosure. With reference to FIG. 9, regarding identifying the blood vessel starting point, in an embodiment, the processor 130 may determine the target blood vessel based on the projection position corresponding to the medical image to perform scene/view classification (step S901). Specifically, according to relevant documents in radiology, different projection positions and/or angles correspond to different target blood vessels. The target blood vessel may include a specific blood vessel intended to view by the doctor or other viewers in the medical image, and may also include the major blood vessel.

Figure 10:
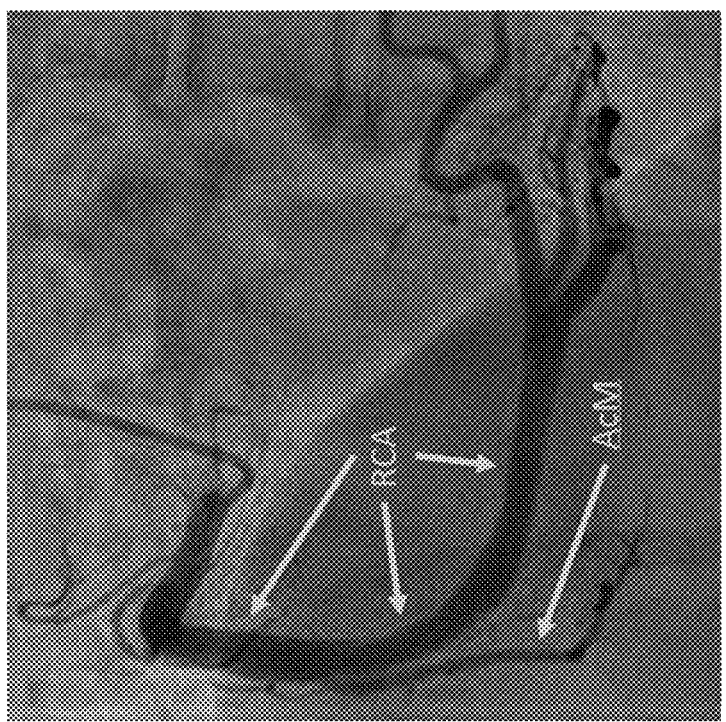
FIG. 10 shows examples of different projection positions.
Figure 10:
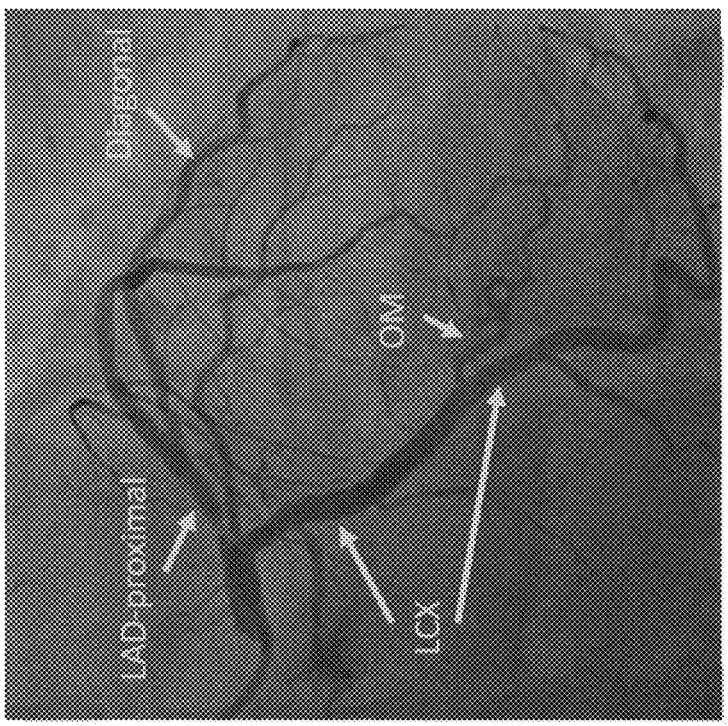

Taking the coronary artery as an example, FIG. 10 shows examples of different projection positions. With reference to FIG. 10, the image on the left is a subcostal view at 10 degrees right anterior oblique (RAO) and 30 degrees caudal, and therein the left circumflex branch LCX, the proximal end of the left anterior descending branch LAD-proximal, the diagonal branch Diagonal, and the obtuse marginal branch OM may be observed. However, the left circumflex branch LCX and the proximal end of the left anterior descending branch LAD-proximal are relatively distinguishable, but the left circumflex branch LCX and the obtuse marginal branch OM are relatively less distinguishable. The image on the right is a view at 10 degree left anterior oblique (LAO) and 30 degrees cranial, and therein the right coronary artery RCA and the acute branch AcM may be observed. Although a large C-shape formed by RCA is clearly exhibited, the distal end thereof may overlap other branches and is relatively less distinguishable. It can be accordingly known that in a specific view, a part of the blood vessels can be clearly distinguished (these blood vessels may serve as the target blood vessels in this view), but another part the blood vessels may overlap others or exhibit unclear contours.

Notably, there are many other views regarding the coronary artery or other parts, and the types of views are not limited by the embodiment of the disclosure.

In an embodiment, the processor 130 may classify the scene/view to which the medical image belongs through a classifier related to the machine learning algorithm, and accordingly reason out the target blood vessel corresponding to the scene/view accordingly. In another embodiment, the processor 130 may adopt other image recognition technologies (e.g., scale-invariant feature transform (SIFT) or edge detection) to reason out the scene/view to which the medical image belongs.

Figure 11:
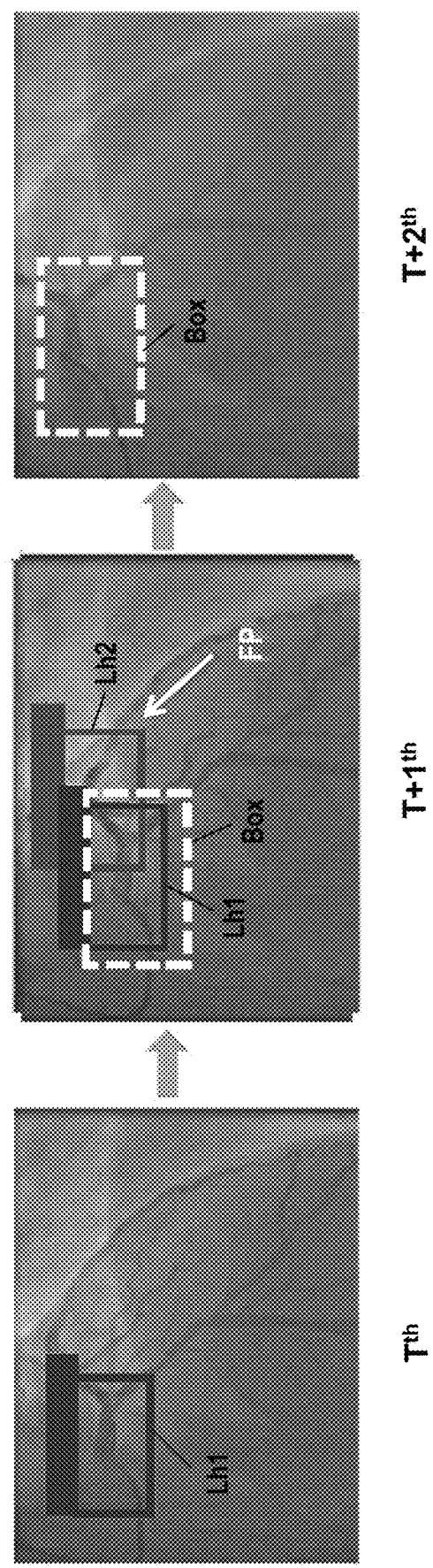
FIG. 11 shows an example of blood vessel starting point detection.

Then, the processor 130 may determine the blood vessel starting point of the target blood vessel of the medical image (step S903). Specifically, based on object detection technologies (e.g., region convolutional neural network (R-CNN), fast R-CNN, or YOLO (You Only Look Once)), the processor 130 may identify the class to which an object in one or more candidate regions in a medical image MI belongs and determine the candidate region of the class of a blood vessel starting point Vh. For example, FIG. 11 shows an example of blood vessel starting point detection. With reference to FIG. 11, in a medical image of a $T^{th}$ frame, a blood vessel starting point Lh1 may be detected.

It should be noted that program codes may be loaded into an application programming interface (API) provided by TensorFlow, PyTorch, Keras, or other libraries to realize object detection.

In an embodiment, the processor 130 may use a target tracking technology (e.g., optical flow) to track the region of the blood vessel starting point, and accordingly reduce detection results as false positive and false negative. Taking FIG. 11 as an example, in a medical image of a $T+1^{th}$ frame, two blood vessel starting points Lh1 and Lh2 may be detected. In addition, through analyzing the medical images of the $T^{th}$ and $T+1^{th}$ frames based on the optical flow, a tracking region Box may be formed (e.g., comparing the pixel displacement and the overlapping size between the regions), and the blood vessel starting point Lh2 may accordingly be regarded as false positive FP. Finally, in a medical image of a $T+2^{th}$ frame, it is possible to retain only the tracking region Box (corresponding to the blood vessel starting point Lh1), and remove the blood vessel starting point Lh2 as false positive FP.

Based on the blood vessel starting point, the processor 130 may map the target blood vessel to the segmentation image corresponding to the detection result R2 (step S905) (i.e., image post-processing). Specifically, the segmentation image corresponding to the detection result R2 includes the pixel belonging to the blood vessel. The processor 130 may adopt object detection technologies (e.g., R-CNN, fast R-CNN, or YOLO) to perform more refined detection on the detection result and the second detection result (e.g., the detection result R2) of the blood vessel starting point. Thereby the blood vessel starting point is determined and accordingly mapped to a corresponding position P on the segmentation image, and a detection result R7 (i.e., a segmentation image where the blood vessel starting point is annotated to the blood vessel) is generated.

After the blood vessel starting point is determined, in the detection result R7, the processor 130 may search for all paths that may possibly be the skeleton among a plurality of paths from the blood vessel end point to the blood vessel starting point. Then, the processor 130 may determine the skeleton of the major blood vessel based on a width and a length of the major blood vessel. For example, at any point in the path, a ratio of the square of the length of the edge to the square of the sum of the width is associated with the path decision. With reference to FIG. 8, finally, the processor 130 generates a detection result R6. The detection result R6 includes a skeleton Sk of the major blood vessel. The skeleton Sk may be the shortest path from the blood vessel end point to the blood vessel starting point.

In some embodiments, the processor 130 may further display the detection results R1-R7 on the display 150 for inspection by the doctor or other viewers. Besides, considering the variance of the blood vessel in the time sequence, the display 150 may display the dynamic change of the blood vessel in real time or offline.

In summary of the foregoing, in the blood vessel detecting apparatus and image-based blood vessel detecting method according to the embodiment of the disclosure, a multi-stage detecting model based on machine learning is provided, and the major blood vessel is further identified. Besides, in the embodiment of the disclosure, reference is also made to the factor of temporal changes. Thereby, the accuracy of blood vessel detection is increased.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. An image-based blood vessel detecting method, comprising: detecting first to-be-evaluated data through a first detecting model to obtain a first detection result, wherein the first detecting model is constructed based on a first machine learning algorithm the first to-be-evaluated data comprises at least one medical image obtained from photographing a blood vessel, and the first detection result output by the first detecting model comprises at least one pixel of the at least one medical image belonging to the blood vessel, and the at least one medical image comprises a plurality of medical images sorted based on a time sequence;
   detecting second to-be-evaluated data through a second detecting model to obtain a second detection result, wherein the second detecting model is constructed based on a second machine learning algorithm the second to-be-evaluated data comprises the first detection result, and the second detection result output by the second detecting model comprises the at least one pixel in the at least one medical image belonging to the blood vessel; and detecting third to-be-evaluated data through a third detecting model to obtain a third detection result, wherein the third detecting model is constructed based on a third machine learning algorithm, the third to-be-evaluated data comprises the second detection result of a current one of the medical images and the second detection result of a previous one of the medical images, the third detection result output by the third detecting model comprises a major blood vessel in the at least one medical image, and the major blood vessel is determined based on a weight that evaluates a lesion complexity of a plurality of blood vessel segments.

2. The image-based blood vessel detecting method according to claim 1, comprising:
   performing image processing on the at least one medical image, wherein the image processing is related to augmentation of a contour of the blood vessel, and the second to-be-evaluated data further comprises the at least one medical image on which the image processing is performed.

3. The image-based blood vessel detecting method according to claim 1, wherein the method, after obtaining the second detection result, further comprises:
   segmenting each of the medical images into a plurality of blood vessel regions belonging to the blood vessel based on the second detection result of the medical images to obtain a plurality of segmentation images;
   determining a displacement of each pixel of the blood vessel regions in the segmentation images based on the time sequence; and
   classifying the blood vessel regions based on a comparison result between the displacement corresponding to each of the blood vessel regions and the blood vessel regions in a previous one of the segmentation images, wherein the comparison result is related to the displacement and an overlapping size between the blood vessel regions.

4. The image-based blood vessel detecting method according to claim 1, wherein the method, after obtaining the third detection result, further comprises:
   determining a skeleton of the major blood vessel based on the second detection result and the third detection result, wherein the skeleton is determined based on a width and a length of the major blood vessel.

5. The image-based blood vessel detecting method according to claim 1, wherein the method, after the second detection result is obtained, further comprises:
   determining a target blood vessel based on a projection position corresponding to the at least one medical image; and
   determining a blood vessel starting point of the target blood vessel of the at least one medical image.

6. The image-based blood vessel detecting method according to claim 5, wherein the method, after determining the blood vessel starting point of the target blood vessel of the at least one medical image, further comprises:
   mapping the target blood vessel to the segmentation image corresponding to the second detection result based on the blood vessel starting point, wherein the segmentation image comprises the at least one pixel belonging to the blood vessel.

7. A blood vessel detecting apparatus, comprising:
   a storage device storing a plurality of program codes; and
   a processor coupled to the storage device and configured to load and execute the program codes to:
   detect first to-be-evaluated data through a first detecting model to obtain a first detection result, wherein the first detecting model is constructed based on a first machine learning algorithm, the first to-be-evaluated data comprises at least one medical image obtained from photographing a blood vessel, and the first detection result output by the first detecting model comprises at least one pixel of the at least one medical image belonging to the blood vessel, and the at least one medical image comprises a plurality of medical images sorted based on a time sequence;
   detect second to-be-evaluated data through a second detecting model to obtain a second detection result, wherein the second detecting model is constructed based on a second machine learning algorithm, the second to-be-evaluated data comprises the first detection result, and the second detection result output by the second detecting model comprises the at least one pixel in the at least one medical image belonging to the blood vessel; and
   detect third to-be-evaluated data through a third detecting model to obtain a third detection result, wherein the third detecting model is constructed based on a third machine learning algorithm, the third to-be-evaluated data comprises the second detection result of a current one of the medical images and the second detection result of a previous one of the medical images, the third detection result output by the third detecting model comprises a major blood vessel in the at least one medical image, and the major blood vessel is determined based on a weight that evaluates a lesion complexity of a plurality of blood vessel segments.

8. The blood vessel detecting apparatus according to claim 7, wherein the processor is further configured to:
   perform image processing on the at least one medical image, wherein the image processing is related to augmentation of a contour of the blood vessel, and the second to-be-evaluated data further comprises the at least one medical image on which the image processing is performed.

9. The blood vessel detecting apparatus according to claim 7, wherein the processor is further configured to:
segment each of the medical images into a plurality of blood vessel regions belonging to the blood vessel based on the second detection result of the medical images to obtain a plurality of segmentation images;
determine a displacement of each pixel of the blood vessel regions in the segmentation images based on the time sequence; and
classify the blood vessel regions based on a comparison result between the displacement corresponding to each of the blood vessel regions and the blood vessel regions in a previous one of the segmentation images, wherein the comparison result is related to the displacement and an overlapping size between the blood vessel regions.

10. The blood vessel detecting apparatus according to claim 7, wherein the processor is further configured to:
determine a skeleton of the major blood vessel based on the second detection result and the third detection result, wherein the skeleton is determined based on a width and a length of the major blood vessel.

11. The blood vessel detecting apparatus according to claim 7, wherein the processor is further configured to:
determine a target blood vessel based on a projection position corresponding to the at least one medical image; and
determine a blood vessel starting point of the target blood vessel of the at least one medical image.

12. The blood vessel detecting apparatus according to claim 11, wherein the processor is further configured to:
map the target blood vessel to the segmentation image corresponding to the second detection result based on the blood vessel starting point, wherein the segmentation image comprises the at least one pixel belonging to the blood vessel.

* * * * *